(12) United States Patent  (10) Patent No.: US 8,624,057 B2
Rowland  (45) Date of Patent: Jan. 7, 2014

(54) ISOPRENOID COMPOUNDS, THEIR ISOLATION AND USE

(75) Inventor: Steven John Rowland, Cornwall (GB)

(73) Assignee: University of Plymouth, Plymouth, Devon (GB)

( * ) Notice: Subject to any disclaimer, the term of this patent is extended or adjusted under 35 U.S.C. 154(b) by 683 days.

(21) Appl. No.: 12/532,349

(22) PCT Filed: Mar. 19, 2008

(86) PCT No.: PCT/GB2008/000976
§ 371 (c)(1),
(2), (4) Date: Jul. 2, 2010

(87) PCT Pub. No.: WO2008/114015
PCT Pub. Date: Sep. 25, 2008

(65) Prior Publication Data
US 2010/0297217 A1   Nov. 25, 2010

(30) Foreign Application Priority Data
Mar. 20, 2007 (GB) .................................. 0705299.6

(51) Int. Cl.
*C07C 69/608* (2006.01)
*C07C 31/27* (2006.01)
*C07C 43/10* (2006.01)
*C07C 55/28* (2006.01)
*A61K 31/00* (2006.01)

(52) U.S. Cl.
USPC ............ 562/498; 560/116; 568/367; 568/420

(58) Field of Classification Search
None
See application file for complete search history.

(56) References Cited

PUBLICATIONS

Lutnaes et al. Organic & Biomolecular Chemistry, 2006, 4, 616-620.*
Smith et al. J. Sep. Sci., 2007, 30, 375-380.*

* cited by examiner

*Primary Examiner* — Yevegeny Valenrod
(74) *Attorney, Agent, or Firm* — Kimberly A. Chasteen

(57) ABSTRACT

There is provided an isoprenoid according to the general formula (I) wherein $R_1$ and $R_2$ are independently selected from H and alkyl; and $R_3$, $R_4$, $R_5$ and $R_6$ are independently selected from groups of the general formula (II) and (III) wherein $R_7$ and $R_8$ each represent a group of general formula $CO-R_9$, in which each $R_9$ is independently selected from H, OH, alkyl and alkoxy groups, or $R_7$ and/or $R_8$ present in $R_3$ and $R_4$ and/or in $R_5$ and $R_6$ combine to form a group of the general formula (IV) wherein $R_{10}$ is selected from OH and alkoxy; or salts thereof. The isoprenoids are of particular use in the preparation of liposomes, for use in the delivery of pharmaceutically active components to a subject human or animal.

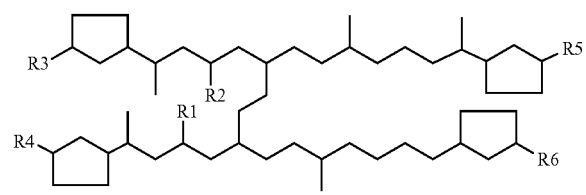

(I)

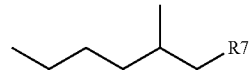

(II)

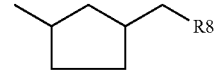

(III)

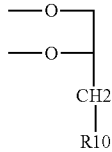

(IV)

22 Claims, 6 Drawing Sheets

ISOPRENOID COMPOUNDS, THEIR ISOLATION AND USE

CROSS REFERENCE TO RELATED APPLICATION

The present application claims priority from PCT Patent Application No. PCT/GB2008/000976 filed 19 Mar. 2008 and GB Patent Application GB0705299.6 filed 20 Mar. 2007.

The present invention relates to certain novel isoprenoid tetraacids, their extraction and isolation, and the use of isoprenoid tetraacids as adjuvants in such applications as vaccine and pharmaceutical preparations and delivery.

Liposomes are closed vesicles comprising a membrane of lipid molecules. Liposomes generally, but not exclusively, contain an aqueous medium within the membrane. Liposomes have been attracting increasing interest as adjuvants in the delivery of active species, such as drugs and other biologically active materials to specific sites within the human or animal body, for example cancer cells. As an example of the specific delivery of antigens in liposomes, reference is made to 'Liposomes Containing Lipid A serve as an Adjuvant for Induction of Antibody and Cytotoxic T-Cell Responses against RTS, S Malaria Antigen', Richards, R. L., et al., Infection and Immunity, June 1998, Pages 2859 to 2865.

U.S. Pat. No. 5,989,587 describes the formation of stable liposomes from lipid extracts of Archaebacteria (Archaea). Lipids disclosed in U.S. Pat. No. 5,989,587 have the following formulae I, II and III:

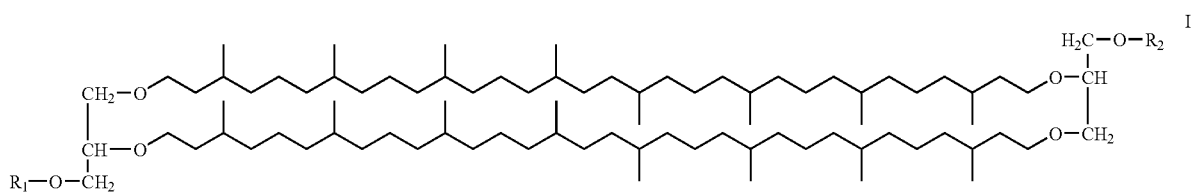

in which $R_1$ is β-gal$_f$- and $R_2$ is α-glc$_p$-(1-2)-β-gal$_f$-;

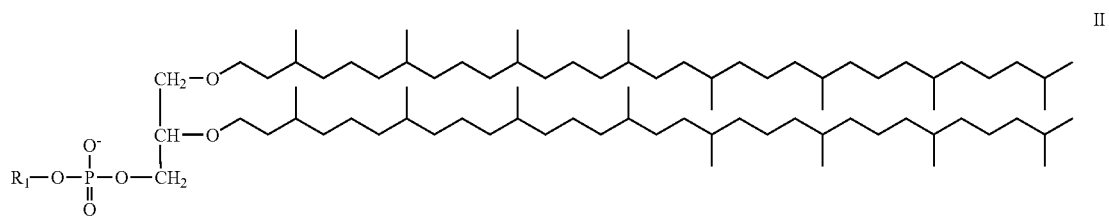

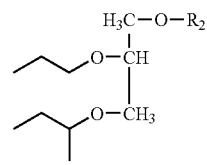

in which $R_1$ is $(CH_3)_2$—N—$C_5O_4H_{10}$— or $(CH_3)_2$—N—$C_5O_4H_{10}$— and $R_2$ is α-glc$_p$-(1-2) -β-gal$_f$-, β-gal$_f$-(1-6)-β-gal$_f$- or β-gal$_f$-; and

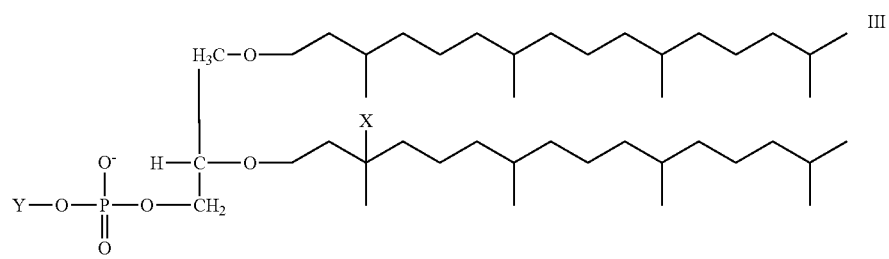

in which X is OH, and Y is ethanolamine or glycerol. Liposomes comprising one or more of the above lipids are disclosed in U.S. Pat. No. 5,989,587, together with a method of their preparation.

Conventional liposomes used in the development of improved delivery systems have been prepared from phospholipids, in some cases mixed with sterols such as cholesterol or other compounds, to improve their stability. More recently, some attention has been turned to the use of ether lipids obtained from archaebacteria. U.S. Pat. Nos. 6,132,789 and 6,403,117 disclose archaeosome compositions and their use in vaccine formulations as adjuvants and/or delivery systems, to enhance the immune response to immunogens in an animal or human. U.S. Pat. No. 6,132,789 and U.S. Pat. No. 6,403,117 also describe the use of the archaeosomes in enhancing the delivery of certain pharmaceuticals to specific cell types and tissues in animals and humans. A liposome composition is disclosed comprising the total polar lipid extract of an Archae bacterium and one or both of coenzyme $Q_{10}$ and an antigen or a pharmaceutical.

Further investigations into the use of lipids extracted from Archae bacteria in the formation of liposomes for use in vaccine and drug delivery are described in 'Archaeosome Vaccine Adjuvants Induce Strong Humoral, Cell-Mediated, and Memory Responses Comparison to Conventional Liposomes and Alum', Krishnan, L. et al., Infection and Immunity, January 2000, Pages 54 to 63; 'Archaeosomes Induce Enhanced Cytotoxic T Lymphocyte Responses to Entrapped Soluble Protein in the Absence of Interleukin 12 and Protect against Tumor Challenge', Krishnan, L. et al., Cancer Research 63, pages 2526 to 2534, May 15, 2003; and 'The potent Adjuvant Activity of Archaeosomes Correlates to the Recruitment and Activation of Macrophages and Dendritic Cells In Vivo', Krishnan, L. et al., The Journal of Immunology, 2001, pages 1885 to 1893.

A range of lipids has been extracted from bacteria from different sources. Liposomes prepared from lipids extracted from mycobacteria and their use as vaccine adjuvants are described in WO 03/011336 and US 2004/0191304 A1. In 'Temperature-dependent variation in the distribution of tetraether membrane lipids of marine Crenarchaeota: Implications for $TEX_{86}$ paleothermometry', Wuchter, C. et al., Paleoceanography, Vol. 19, PA4028, a range of lipids having the following formulae are disclosed as having been extracted from certain Crenarchaeota bacteria cultivated from sea water obtained from the North Sea:

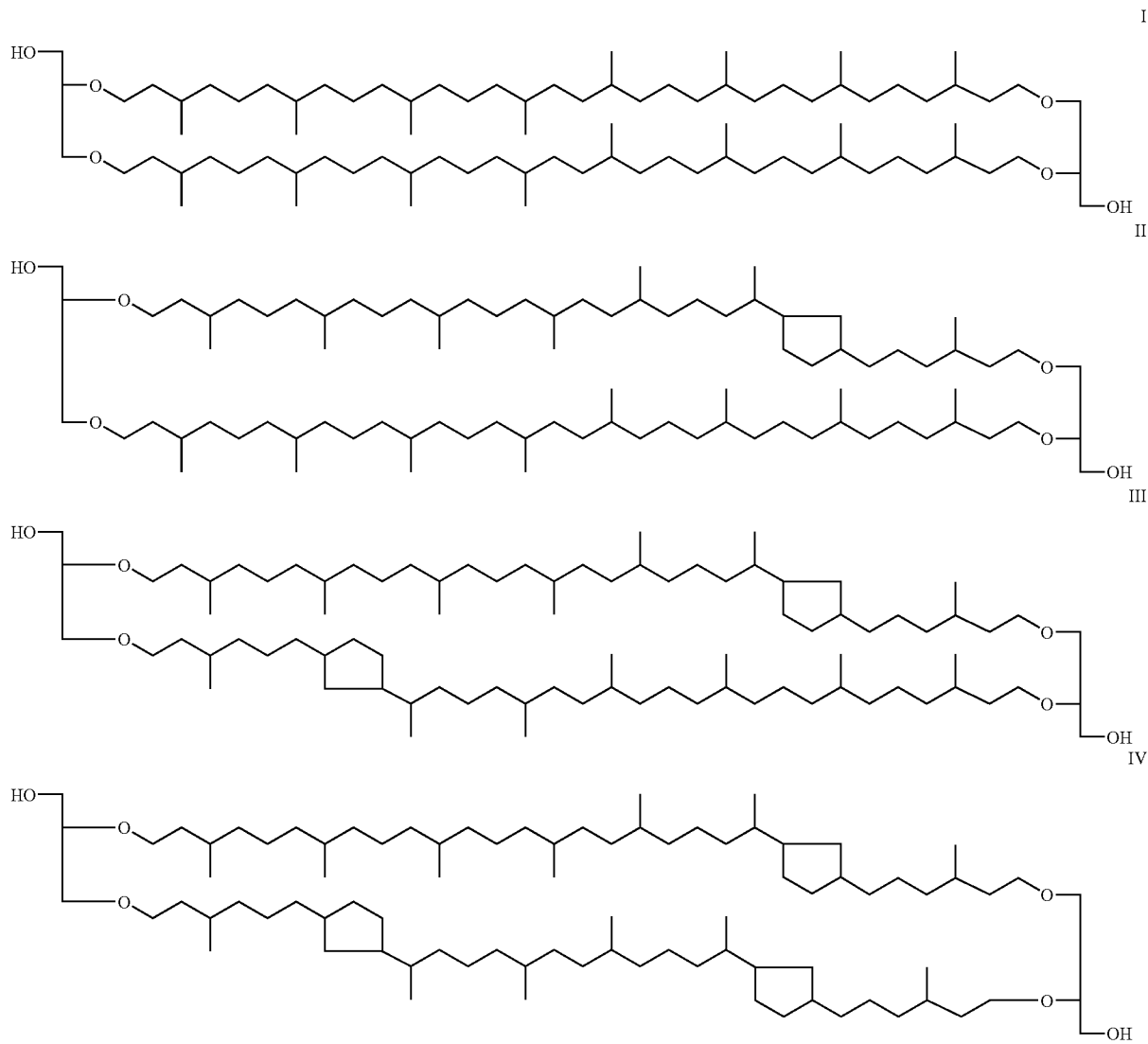

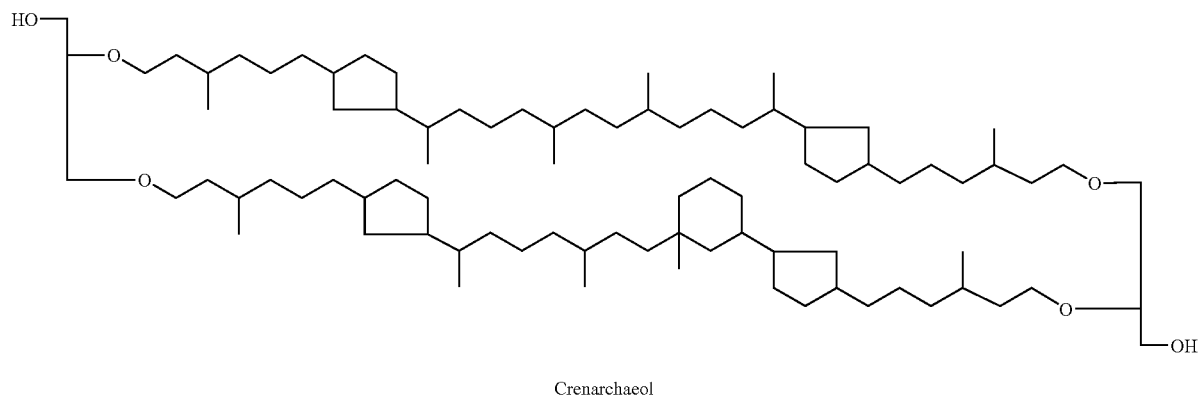

Crenarchaeol

Recently, certain investigations have elucidated the structure of components of naphthenate deposits in crude oil processing. Certain crude oils with a high naphthenic acid content present problems with their transport in pipelines and their processing due to the deposition of naphthenates, in particular calcium salts. The salts are deposited in pipelines and processing equipment as sludge, which if allowed to accumulate will compromise the oil processing and transport operations. The increasing need for crude oil and its derivatives has required the production of ever increasing volumes of high naphthenic acid crude oils. As a result, much time and effort is devoted to the removal of such deposits from processing equipment. An investigation into the compounds responsible for naphthenate deposition has identified archaeal $C_{80}$ isoprenoid tetraacids as being responsible components. In 'Archael $C_{80}$ isoprenoid tetraacids responsible for napthenate deposition in crude oil processing', Lutnaes, B. F. et al., Org. Biomol. Chem., 2006, 4, pages 616 to 620, a tentative structure for a six ring tetraacid (6:17, 10:18, 10':18'; 6":17"; 10":18", 10'": 18'")-hexacyclo-20-bis-16,16'-biphytane-1,1',1",1'"-tetracarboxylic acid was proposed as follows:

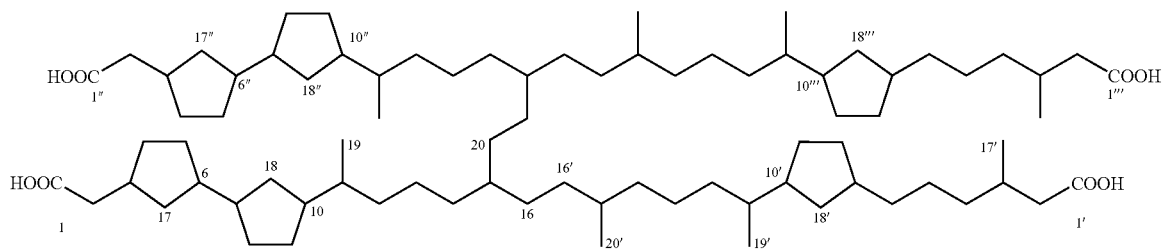 [SMILES: CC(CCCC(C)C1CCC(CCCC(C)CC(=O)O)C1)CCC(CCCC(C)C1CCC(C2CCC(CC(=O)O)C2)C1)CCC(CCCC(C)C1CCC(C2CCC(CC(=O)O)C2)C1)CCC(C)CCCC(C)C1CCC(CCCC(C)CC(=O)O)C1]

Most recently, Smith, B. E. et al., in 'Analysis of 'ARN' naphthenic acids by high temperature gas chromatography and high performance liquid chromatography', Journal of Separation Science, 2007, 30(3) pages 375 to 380, have provided the following tentative structures for certain isoprenoid tetraacids liberated from oil fields in West Africa and the Heidrun oil field in the Norwegian Sea:

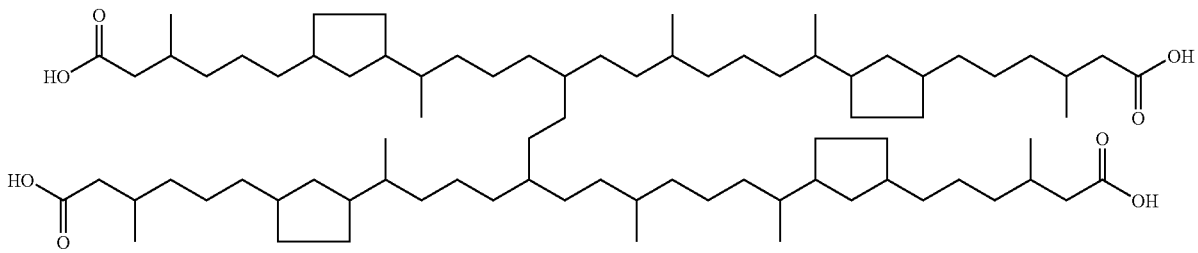

-continued

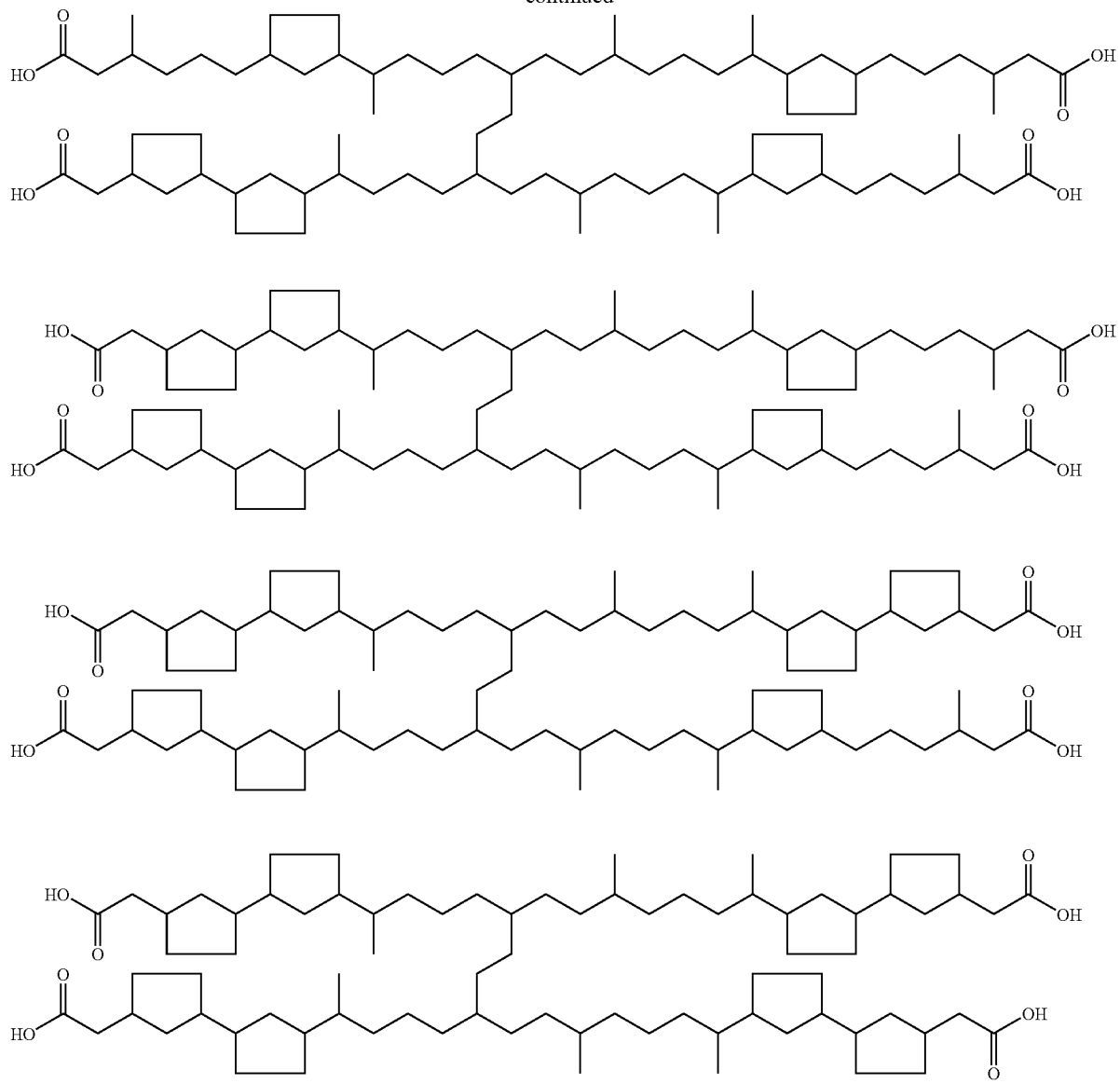

A range of $C_{80}$ and higher isoprenoid tetraacids have now for the first time been isolated and their structures determined and confirmed. These isoprenoid tetraacids have applications in the preparation of liposomes for use in the delivery of pharmaceuticals and other agents to human or animal subjects.

Accordingly, in a first aspect, the present invention provides an isoprenoid according to the general formula (I):

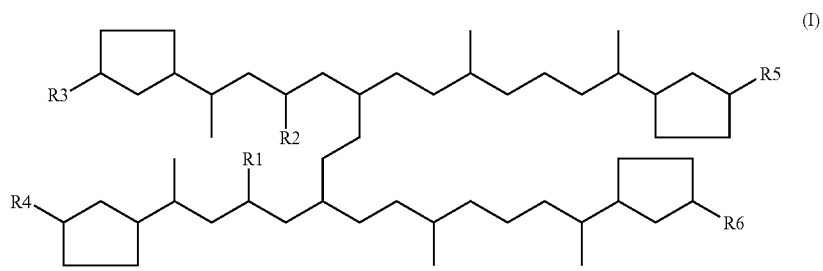

wherein $R_1$ and $R_2$ are independently selected from H and alkyl; and $R_3$, $R_4$, $R_5$ and $R_6$ are independently selected from groups of the general formula (II) and (III):

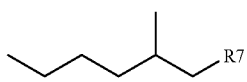

(II)

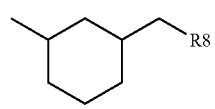

(III)

wherein $R_7$ and $R_8$ each represent a group of general formula CO—$R_9$, in which each $R_9$ is independently selected from H, OH, alkyl and alkoxy groups, or $R_7$ and/or $R_8$ present in $R_3$ and $R_4$ and/or in $R_5$ and $R_6$ combine to form a group of the general formula (IV):

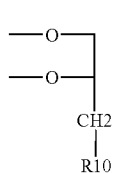

(IV)

wherein $R_{10}$ is selected from OH and alkoxy; or salts thereof.

Alkyl groups present in the compounds of general formula (I) are preferably lower alkyl groups, that is alkyl groups having from 1 to 10 carbon atoms, more preferably from 1 to 6 carbon atoms, especially from 1 to 4 carbon atoms. Methyl is a particularly preferred alkyl group.

Alkoxy groups present in the compounds of general formula (I) are preferably lower alkoxy groups, that is alkoxy groups having from 1 to 10 carbon atoms, more preferably from 1 to 6 carbon atoms, especially from 1 to 4 carbon atoms. Methoxy is a particularly preferred alkoxy group.

In one embodiment, preferred compounds of general formula (I) are those in which both $R_1$ and $R_2$ are both hydrogen.

In the alternative, preferred compounds are those in which $R_2$ is hydrogen and $R_1$ is alkyl, most preferably an alkyl group having from 1 to 4 carbon atoms, especially methyl.

In a further preferred alternative, both $R_1$ and $R_2$ are alkyl, preferably lower alkyl having from 1 to 4 carbon atoms, with compounds in which both $R_1$ and $R_2$ are methyl being particularly preferred.

In a further embodiment, preferred compounds are those in which $R_3$ and $R_5$ are both groups of the general formula (II). In the alternative, preferred compounds are those in which $R_3$ and $R_4$ are both groups of the general formula (II). A further group of preferred compounds are those in which both $R_3$ and $R_6$ are both groups of the general formula (II). One particularly preferred group of compounds are those in which all of $R_3$, $R_4$, $R_5$ and $R_6$ are groups of the general formula (II).

In a still further embodiment, preferred compounds are those in which $R_5$ and $R_6$ are both groups of the general formula (III). In the alternative, preferred compounds are those in which $R_4$ and $R_6$ are both groups of the general formula (III). A further group of preferred compounds are those in which both $R_4$ and $R_5$ are both groups of the general formula (II). One particularly preferred group of compounds are those in which all of $R_3$, $R_4$, $R_5$ and $R_6$ are groups of the general formula (III).

In compounds comprising one or more groups of the general formula (II), $R_7$ is preferably a group of general formula CO—$R_9$, in which $R_9$ is OH or an alkyl group, most preferably an alkyl group having from 1 to 4 carbon atoms, especially methyl. In compounds comprising more than one group of the general formula (II), each $R_7$ may be independently selected from the aforementioned groups, or some or all of the $R_7$ moieties may be the same. It is preferred that all $R_7$ groups present in the compounds are the same, that is, are groups of the general formula CO—$R_9$, in which all $R_9$ moeities are hydrogen, hydroxy, or the same alkyl or alkoxy group.

In compounds comprising one or more groups of the general formula (III), $R_8$ is preferably a group of general formula CO—$R_g$, in which $R_9$ is OH or an alkyl group, most preferably an alkyl group having from 1 to 4 carbon atoms, especially methyl. In compounds comprising more than one group of the general formula (II), each $R_8$ may be independently selected from the aforementioned groups, or some or all of the $R_8$ moieties may be the same. It is preferred that all $R_8$ groups present in the compounds are the same, that is, are groups of the general formula CO—$R_9$, in which all $R_9$ moeities are hydrogen, hydroxy, or the same alkyl or alkoxy group.

Compounds in which one or both of $R_3$ and $R_4$ and $R_5$ and $R_6$ comprise $R_7$ and/or $R_8$ moeties combined to form a group of the general formula (IV) are ethers.

When both $R_3$ and $R_4$ and $R_5$ and $R_6$ have $R_7$ and/or $R_8$ moeities combined to form groups of general formula (IV), the compounds are tetraethers. When present, the or each $R_{10}$ is preferably OH. As noted above, the or each $R_{10}$ may be an alkyl group, in which case $R_{10}$ is preferably a lower alkyl group having from 1 to 4 carbon atoms, with methyl being especially preferred. In tetraether compounds comprising two $R_{10}$ groups, the two groups may be the same or different. Preferred compounds are those in which both $R_{10}$ groups are the same.

In compounds of the present invention, the end groups $R_7$ and/or $R_8$ of each of $R_3$, $R_4$, $R_5$ and $R_6$ may be the same or different. For example, in the compounds in which some or all of the groups $R_3$, $R_4$, $R_5$ and $R_6$ represent groups of general formulae (II) or (III) in which either $R_7$ or $R_8$ represent groups of the general formula CO—$R_9$ in which all $R_9$ moeities are OH, the compounds may be mono-carboxylic acids, di-carboxylic acids, tert-dicarboxylic acids or tetra-carboxylic acids. In the present invention, the preferred compounds are those in which all of $R_7$ and $R_8$ represent the same group, with $R_9$ representing methyl or OH being preferred. Tetra-carboxylic acids are particularly preferred compounds of the present invention.

A further preferred group of compounds falling within the present invention are the glyceryl tetraethers, as described above, that is compounds of general formula (I) in which $R_3$ and $R_4$ comprise groups $R_7$ and/or $R_8$ combined to form a first group of general formula (IV) and $R_5$ and $R_6$ comprise groups $R_7$ and/or $R_8$ combined to form a second group of general formula (IV).

Particularly preferred compounds of the general formula (I) are those having the following structures:
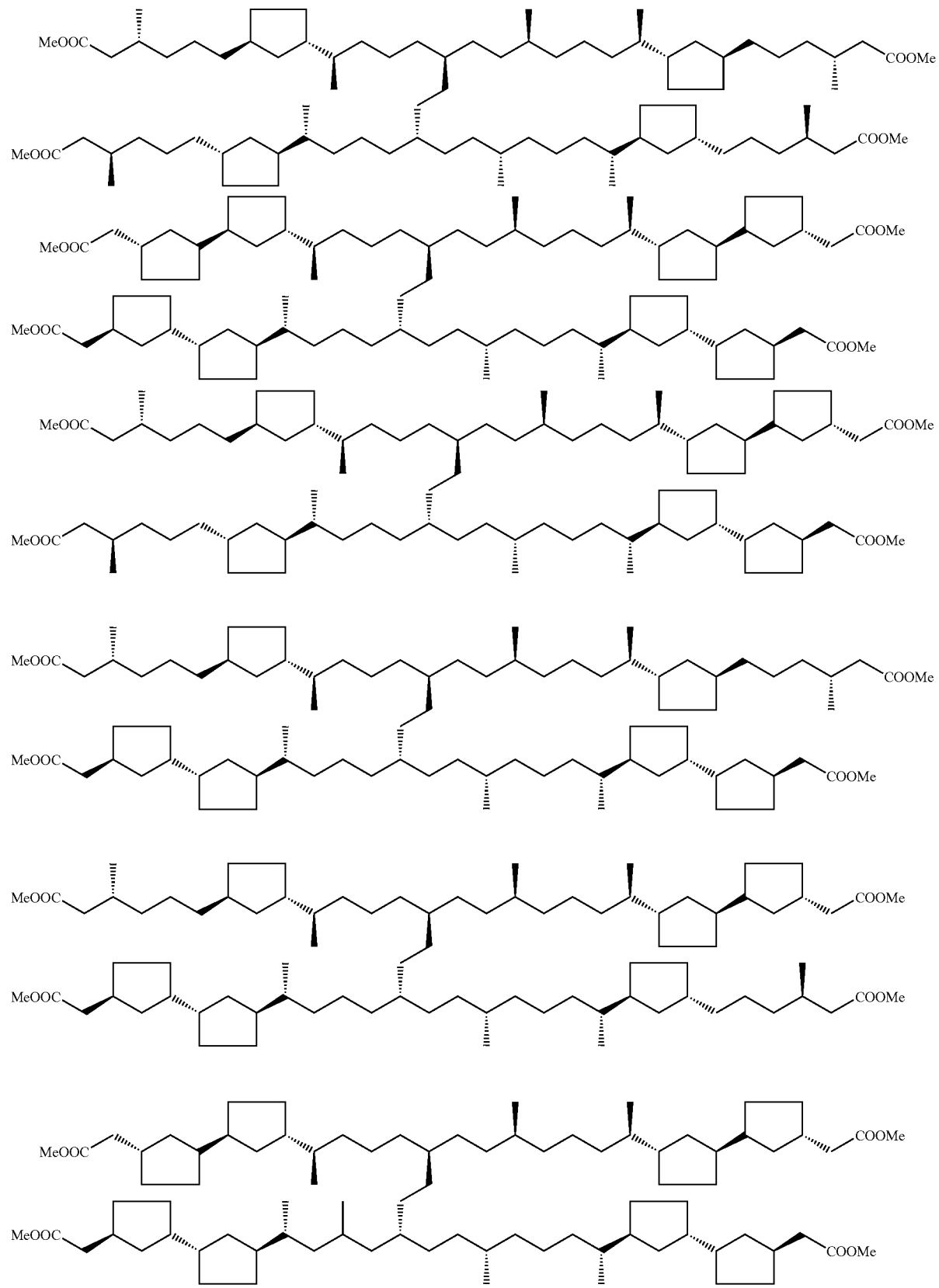

-continued

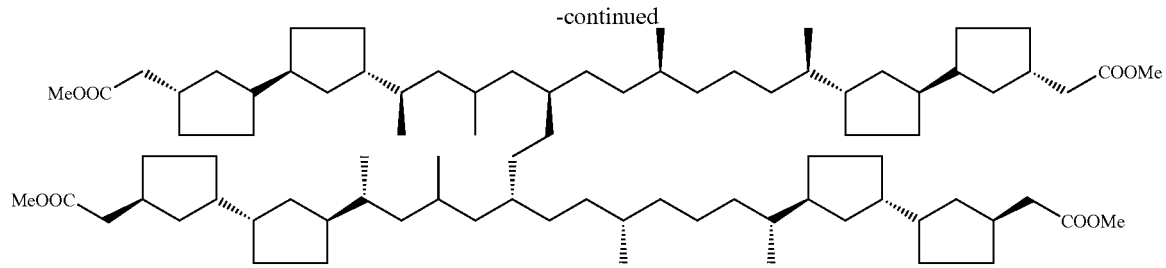

Also preferred are the tetraacid, tetra-alcohols and tetra-methyl ethers corresponding to the above listed compounds. Further preferred compounds are the glyceryl tetraethers corresponding to each of the above listed compounds.

When the compounds of the present invention include one or more carboxylic acid groups, the present invention also includes the salts thereof. Examples of salts include salts of alkali and alkaline earth metals, and ammonium. Preferred salts are potassium, sodium and calcium salts.

In a further aspect, the present invention provides provides an isoprenoid according to the general formula (I):

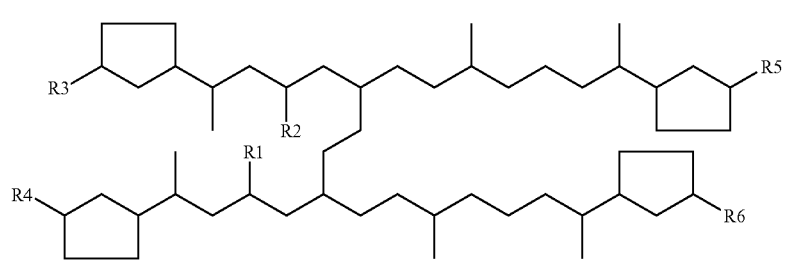

(I)

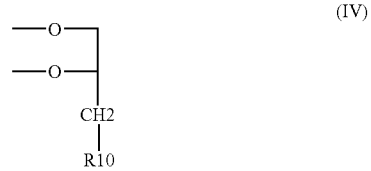

(IV)

wherein $R_{10}$ is selected from OH and alkoxy;

wherein $R_1$ and $R_2$ are independently selected from H and alkyl; and $R_3$, $R_4$, $R_5$ and $R_6$ are independently selected from groups of the general formula (II) and (III):

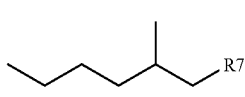

(II)

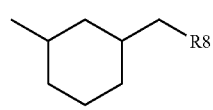

(III)

wherein $R_7$ and $R_8$ each represent a group of general formula CO—$R_9$, in which each $R_9$ is independently selected from H, OH, alkyl and alkoxy groups, or $R_7$ and/or $R_8$ present in $R_3$ and $R_4$ and/or in $R_5$ and $R_6$ combine to form a group of the general formula (IV):

with the proviso that when $R_6$ is a group of general formula (II) in which $R_7$ is a group of general formula CO—$R_9$ and $R_9$ is hydrogen:

$R_3$, $R_4$ and $R_5$ are not all a group of general formula (II) in which $R_7$ is a group of general formula CO—$R_9$ and $R_9$ is hydrogen;

$R_4$ is not a group of general formula (III) in which $R_8$ is a group of general formula CO—$R_9$ and $R_9$ is hydrogen, and $R_3$ and $R_5$ are not both a group of general formula (II) in which $R_7$ is a group of general formula CO—$R_9$ and $R_9$ is hydrogen;

$R_3$ and $R_4$ are not both a group of general formula (III) in which $R_8$ is a group of general formula CO—$R_9$ and $R_9$ is hydrogen, and $R_5$ is not a group of general formula (II) in which $R_7$ is a group of general formula CO—$R_9$ and $R_9$ is hydrogen; and $R_3$, $R_4$ and $R_5$ are not all a group of general formula (III) in which $R_8$ is a group of general formula CO—$R_9$ and $R_9$ is hydrogen; and with the proviso that $R_3$, $R_4$, $R_5$, and $R_6$ are not all a group of general formula (III) in which $R_8$ is a group of general formula CO—$R_9$ and $R_9$ is hydrogen.

Preferred compounds are as described hereinbefore, subject to the aforementioned provisos. Particularly preferred compounds according to this aspect of the present invention are those having the following structures:

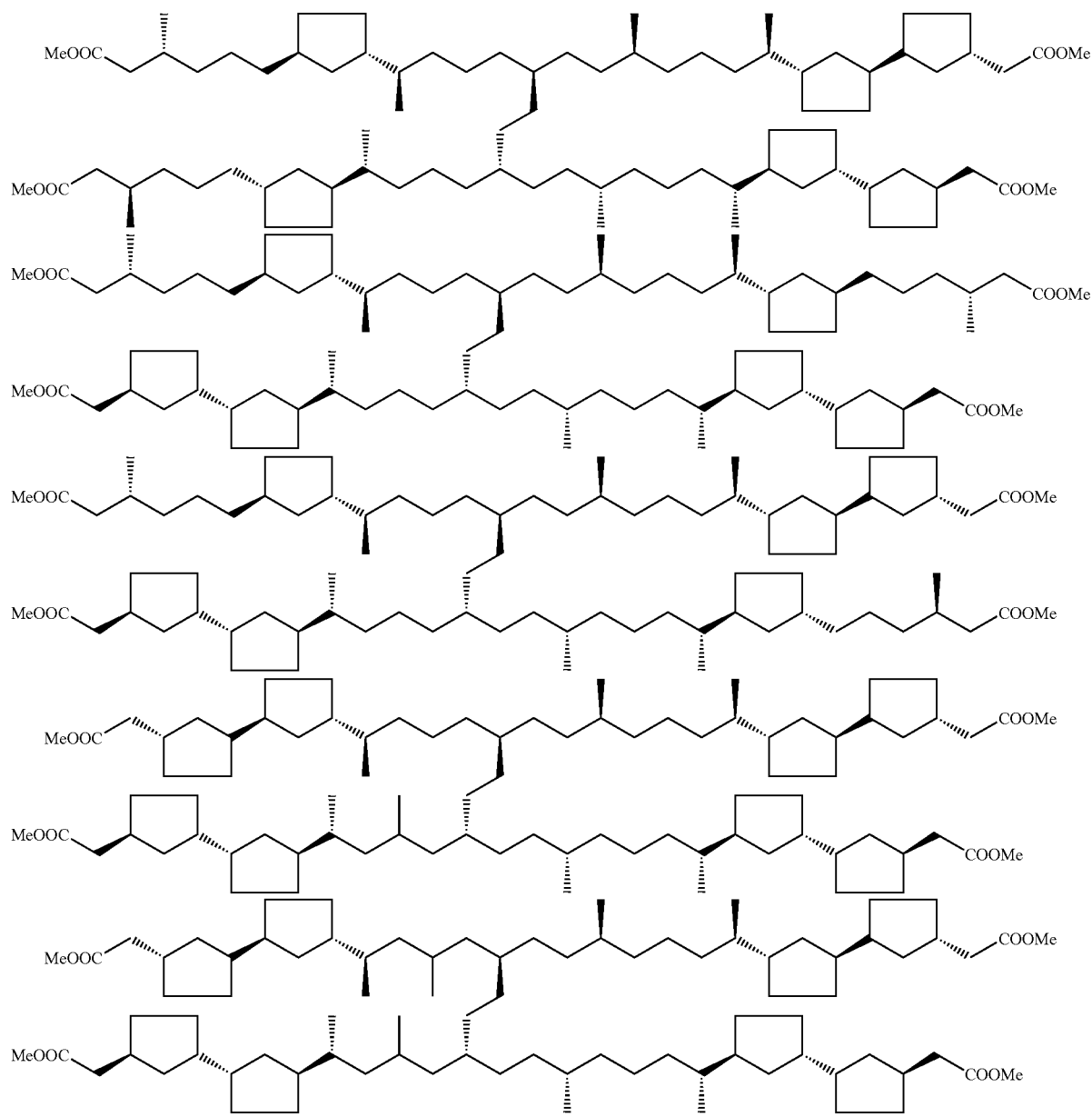

The compounds of general formula (I) may be obtained by methods known in the art. In particular, as noted, tetraacid and tetra-ester compounds of the general formula (I) are naturally occurring in crude oil, in particular crude oils having a high naphthenic acid content. Examples of high naphthenic crude oils include those obtained from oilfields in West Africa, the North Sea and the Norwegian Sea. Crude oil produced in the Heidrun field of the Norwegian Sea has been found to contain significant amounts of compounds of the general formula (I). The compounds of the present invention may be extracted from crude oil using techniques known in the art. Suitable methods for obtaining the compounds include base extraction or saponification, separation using silica gel impregnated potassium hydroxide, separation using a cyano-modified silica column following elution with non-polar solvents. In addition, non-aqueous ion exchange methods can be employed to extract the compounds from crude oil in known manner. Examples of suitable methods for the isolation of compounds of the present invention from crude oil are disclosed by Jones, D. M. et al., 'Determination of Naphthenic Acids in Crude Oils using Non-aqueous Ion Exchange Solid-Phase Extraction', Anal. Chem. 2001, 73, pages 703 to 707, and Smith, B. E. et al., in 'Analysis of 'ARN' naphthenic acids by high temperature gas chromatography and high performance liquid chromatography', discussed hereinbefore.

A particularly preferred method for the isolation of compounds of the present invention from crude oil is disclosed by Lutnaes, B. F., et al., 'Archael $C_{80}$ isoprenoid tetraacids responsible for naphthenate deposition in crude oil processing', Org. Biomol. Chem., 2006, 4, pages 616 to 620. In this method, naphthenic acids are isolated from deposits formed from crude oil, for example as may form in pipelines and equipment processing crude oil. The naphthenic acids may be isolated by acid ion-exchange resin (Acid-IER) techniques.

Suitable Acid-IER techniques are known in the art, for example as disclosed by Mediaas, H., et al., Proceedings—SPE 5$^{th}$ International Oilfield Scale Symposium, Aberdeen, SPE 80404, 2003.

As a first step, the deposit is washed in a suitable organic solvent, preferably a non-polar solvent, for example toluene, in order to remove crude oil residue and any oil-soluble components. Completion of the washing stage may be determined by monitoring the colour of the solvent, with washing being complete when there is little or no change in the colour of the solvent during contact with the deposits. Thereafter, the naphthenate may be dissolved by contact with a mixture of a suitable organic solvent, most preferably a non-polar solvent, and an aqueous solution of an inorganic acid, for example a mixture of toluene and hydrochloric acid. This step converts the chemically bound naphthenates to free acid monomers, dissolved in the organic phase, with the counter ions remaining in the aqueous phase. The naphthenic acids may be separated from other polar compounds present in the organic phase using ion-exchange using a suitable resin, for example QAE Sephadex A-25. Such resins are well known in the art and commercially available. The remaining solvent may be removed from the naphthenic acids by conventional evaporation and drying techniques, for example using a rotary evaporator and oven drying.

The compounds of the present invention are extracted from the aforementioned crude oils in the form of acids and/or esters, typically tetraacids and tetra-esters. Compounds of the present invention in which one or more of $R_7$ and $R_8$ are hydrogen may be prepared from the corresponding acid or ester by methods well known in the art. One suitable method is to react the acid or ester with a suitable reducing agent. Reducing agents active in such reactions are well known in the art and include lithium aluminium hydride ($LiAlH_4$) and sodium borohydride ($NaBH_4$).

It has been found that isoprenoid tetraacids, in particular $C_{80}$, $C_{81}$ and $C_{82}$ isoprenoid tetraacids and their equivalent esters, ethers and alcohols may be used in the preparation of liposomes for the enhanced delivery of pharmaceuticals and other active agents to human and animal subjects, in particular in the enhanced delivery of such agents to target cells within the human or animal body.

Accordingly, in a further aspect, the present invention provides a liposome composition comprising an isoprenoid lipid, in particular an acid, an ester thereof or a corresponding ether, glyceryl ether or alcohol thereof, and a pharmaceutically active component.

The isprenoid lipid used in the preparation of the liposome of the present invention is preferably a $C_{80}$, $C_{81}$ or $C_{82}$ isoprenoid lipid. It has been found that these compounds are prepared by certain strains of Archaea, in particular the hyperthermophilic Archaea capable of living and propagating at temperatures above about 90° C. Particularly preferred isoprenoid lipids are the so-called ARN lipids, in particular ARN tetraacids. These compounds are characterised by having a cross-branched or 'H' shaped structure of the general formula (V):

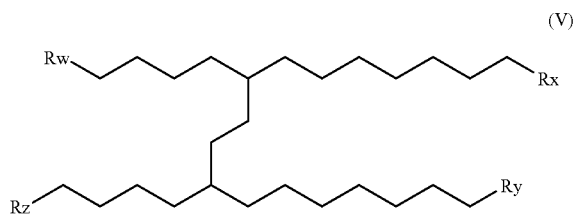

(V)

in which $R_W$, $R_x$, $R_y$ and $R_z$, are each independently selected from an aliphatic or alicyclic group, for example groups of general formulae (II) and (III) defined hereinbefore, or $R_W$ and $R_z$, and/or $R_x$ and $R_y$ are combined to form a di-ether group, for example groups of the general formula (IV) defined hereinbefore, or salts thereof.

Preferred compounds of the general formula (IV) are acids, in particular tetraacids and their salts. Examples of preferred salts at alkali metal and alkaline earth metal salts, including potassium, sodium, and calcium salts. Other salts may be suitable for use in the liposome composition.

Preferred compounds for the preparation of the liposome compositions of the present invention are the compounds of general formula (I) as hereinbefore defined according to the first and second aspects of the present invention.

Liposome compositions of the present invention may be prepared using techniques known in the art. In a further aspect, the present invention provides a method for preparing a liposome comprising hydrating an isoprenoid acid, in particular an isoprenoid acid as hereinbefore defined and described, or a salt thereof in an aqueous medium. Isoprenoid tetraacids and their salts are particularly preferred compounds for forming the liposomes.

The isoprenoid acid or its salt may be hydrated using water, in particular deionized water, or a buffered aqueous solution of suitable salts, for example a buffered saline solution, in particular a phosphate buffered saline solution. The isoprenoid acid or salt thereof is preferably dried before hydration, for example using known techniques, such as contact with a stream of an inert gas, such as nitrogen.

The aqueous mixture of the isoprenoid acid or the salt thereof may be agitated by suitable techniques to produce the liposomes. Suitable techniques for agitation include sonication, in particular applying ultrasound, or by extruding the aqueous mixture.

The structure of the lipsome will vary according to the method of agitation applied to the aqueous mixture of the isoprenoid acids. Low shear methods of agitation, such as low shear sonication, result in liposomes have a multilayered or multilamellar structure. At higher rates of shear, the liposomes are produced with a single layer of lipid, that is unilamellar. Multilamellar liposomes may be reduced in size, for example to unilamellar liposomes by appropriate shearing of the mixture. The liposomes of the present invention may be multilamellar or unilamellar in structure.

The temperature of the aqueous mixture may be adjusted as required during the preparation of the liposomes. The liposomes of the present invention are preferably formed at elevated temperatures, in particular temperatures greater than 30° C., more preferably greater than 50° C., especially in the range of from 65 to 75° C.

The pharmaceutically active component of the liposome of the present invention is within the aqueous phase disposed within the liposome. The active component may be added to the aqueous mixture before or after agitation and formation of the liposome. Alternatively, the active component may be added during a re-hydration procedure following formation and drying of the initial liposomes. In this way, the active component composition of the aqueous phase contained within the liposome is the same as the composition of the aqueous mixture.

The liposomes of the present invention may comprise any suitable pharmaceutically active component. In this respect, the term 'pharmaceutically active component' is a reference to any compound, component or substance that is required to be delivered to the cells of the human or animal body. The liposomes of the present invention are particularly suitable for containing antigens, in particular proteins, and vaccines for promoting, modifying or modulating the immune response of the subject. Suitable active ingredients for inclusion in the liposomes of the present invention include that act to protect the subject from infection and the development of cancers. The liposomes of the present invention may comprise one or a plurality of pharmaceutically active components.

In a further aspect, the present invention provides the use of a liposome as hereinbefore defined in the delivery of a pharmaceutically active ingredient to a subject. The liposome is of particular use in the delivery of active ingredients, in particular antigens, for modifying or modulating the immune response of the subject, in particular to increase the resistance of the subject to infection or the development of cancers.

Embodiments of the present invention will now be described, by way of illustration only, in the following specific examples, having reference to the accompanying figures, in which.

EXAMPLES

Example 1

Isolation of Methylated Tetraacids

Figure 1A:
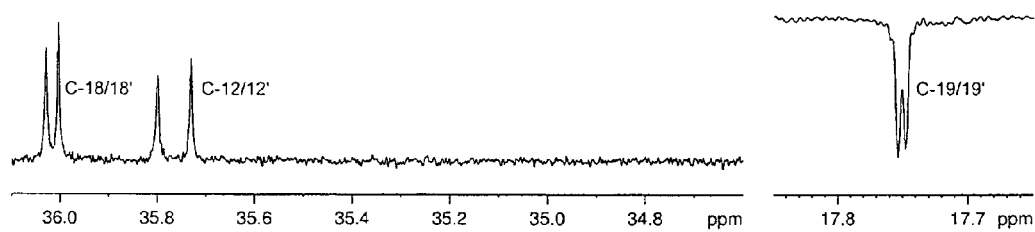
FIGS. 1a, 1b and 1c are graphs of NMR spectral data for a compound of the present invention having a tetracyclic structure.

Methylated tetraacids, isolated from samples of crude oil obtained from oil fields in West Africa and from the Heidrun field in the Norwegian Sea, were obtained from the authors of 'Archael $C_{80}$ isoprenoid tetraacids responsible for napthenate deposition in crude oil processing', Lutnaes, B. F. et al., Org. Biomol. Chem., 2006, 4, pages 616 to 620.

A calcium naphthenate deposit from a crude oil produced in a field in the UK sector of the North Sea was obtained from GB Group Plc. Acids were isolated by the following procedure The deposit was washed in toluene to remove crude oil and oil-soluble fractions by repeated contact with toluene. The washing was continued and repeated until the toluene phase appeared almost clear after contact with the deposit. The remaining solid deposit was contacted with a mixture (2:1 volume) of toluene and hydrochloric acid (1M HCl solution in water). Naphthenate ions were converted to free acid moieties and dissolved in the toluene phase. Calcium ions remained in the aqueous phase. Thereafter, naphthenic acids were selectively isolated from the organic phase using ion-exchange techniques (QAE Sephadex A-25 ion-exchange resin, ex. GE Healthcare Biosciences Ltd., England; ion exchange group: diethyl(2-hydroxy-propy)amino ethyl). The solvent was removed from the naphthenic acids by evaporation in a rotary evaporator at 60° C., followed by drying in an oven at 60° C.

The acids isolated were each subjected to the following procedure:

An aliquot (10 mg) of the isolated acid was dissolved in tetrahydrofuran (THF) (1 ml, HPLC grade, ex. Rathburn Chemicals, Walkerburn, Scotland). $BF_3$-methanol (2 ml, 10% w/w, ex. Supelco, Sigma-Aldrich, UK) was added and the resulting mixture was sealed in a 5 ml reaction vial. The contents of the vial were heated to 60° C. and held at this temperature for 3 hours. Diethyl ether (15 ml, HPLC grade, ex. Rathburn Chemicals, Walkerburn, Scotland) was added and the resulting mixture washed with a saturated sodium chloride solution (3×10 ml). The phases were allowed to separate and the organic phase was decanted and subsequently dried over anhydrous sodium sulphate ($Na_2SO_4$, ex. Fisher Scientific, UK). The resulting product was taken to dryness under reduced pressure.

The product obtained was methylated by the addition of methanol and $BF_3$-diethyl etherate heating in dioxane. The resulting methylated product was fractionated to produce three samples A, B and a heavier fraction. The heavier fraction was subjected to further separation and enrichment using semi-preparative high pressure liquid chromatography (HPLC), to yield samples C, D and E, as follows:

A 25 cm×4.6 mm ZORBAX $NH_2$HPLC column (ex. Hewlett Packard, UK) was fitted to an Agilent series HPLC with an evaporative light scattering detector (ELSD; PL-ELS 1000µ, ex. Polymer Laboratories, UK). The mobile phase used was an isocratic mixture of cyclohexane (55%, ex. Rathburn Chemicals, Walkerburn, Scotland) and dicholormethane (45%, ex. Rathburn Chemicals). Data recording and integration were carried out using Stratos LC software (V 4.0, ex. Polymer Laboratories).

Example 2

Analysis of Isolated Acids

The products obtained following the procedures of Example 1 were subject to analysis using high field NMR spectroscopy. A Bruker Avance 600 NMR instrument equipped with a TCI CryoProbe was employed to obtain the 600 MHz $^1$H and DEPT 135 spectra of all samples A to E obtained in Example 1. NOESY, $^{13}$C, multiplicity-edited HSQC, HMBC and H2BC[11] spectra of the sample B were also obtained using the same instrument. 2D HSQC-TOCSY (75 ms mixing time) spectra for samples D and E were also obtained using the Bruker Avance instrument. A Varian Inova 800 NMR instrument fitted with a TXI probe was used to obtain 800 MHz $^1$H and $^1$H-$^{13}$C HSQC spectra of all samples A to E.

All spectra were recorded at 298 K in $CDCl_3$. The signals were calibrated against residual $CHCl_3$ at 7.27 ppm for $^1$H and 77.2 ppm for $^{13}$C.

Processing and analysis of all spectra were performed using the Bruker TopSpin 1.3 software. All 2D spectra were zero-filled in both dimensions. In addition, forward linear prediction was employed in the indirect dimension.

Mass Spectrometry (MS) analysis of the isolated samples was carried out using a Finnigan Mat LCQ™ bench top mass spectrometer (ex. ThermoFinnigan, San Jose, Calif., USA). The spectrometer was fitted with an electrospray interface. Data were acquired and processed with Xcalibur 1.0 spl software. The infusion of surrogates was carried out using a built-in syringe pump with a Hamilton 1725N (250 µl) syringe (ex. Reno, Calif., USA). Analytes were infused at 3.0 l/min (methanol/formic acid, 99.9:0.1 v/v). The spectrometer was operated with a source voltage +/−4.5 kV, capillary voltage +/−0-50 kV, capillary temperature of 200° C., nitrogen sheath gas flow. All spectral data were recorded and averaged over a 1 minute acquisition time.

Results of Analysis

Sample A

Figure 1B:
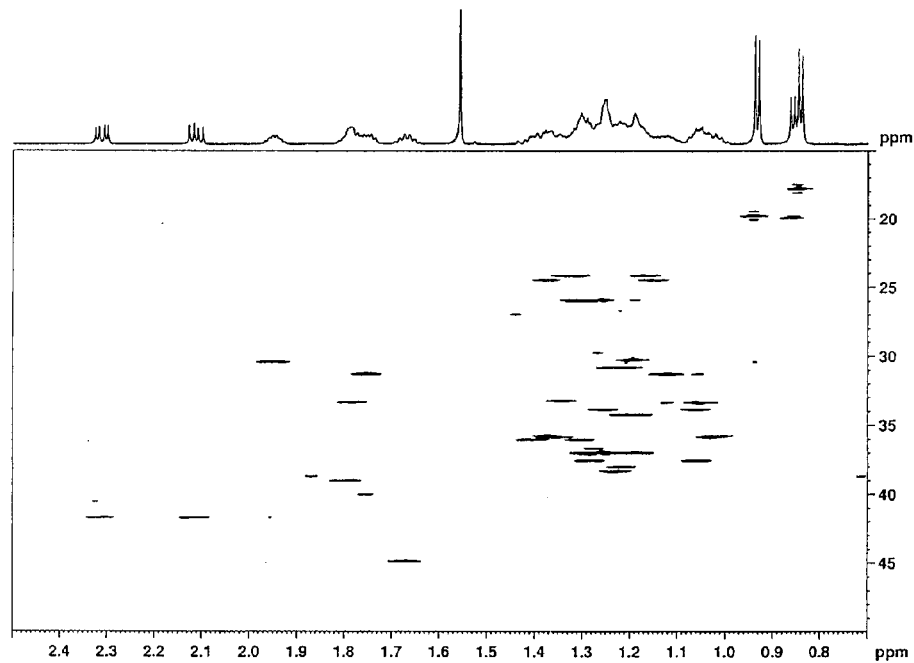
Figure 1C:
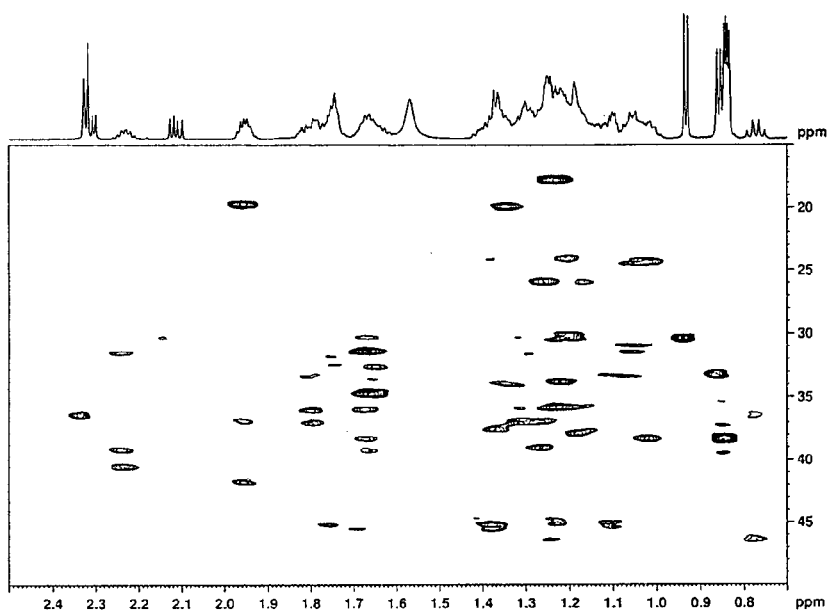
Figure 1D:
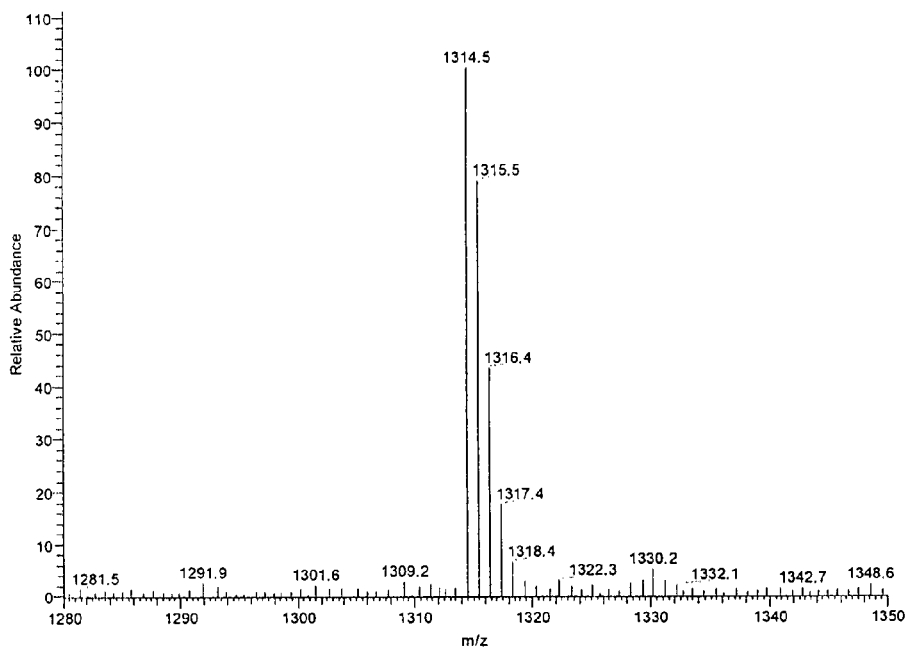
FIG. 1d is a graph of ESI MS data for the compound of FIGS. 1a to 1c.

The NMR data (800 MHz, CDCl$_3$, 298 K) for sample A are set out in Table 1. The NMR spectra (150 MHz DEPT 35, CDCl$_3$, 298 K) for sample A are shown in FIG. 1a. The HSQC spectra (800 MHz, CDCl$_3$, 298 K) for sample A are shown in FIG. 1b. The H$_2$BC spectrum (600 MHz, 298 K, CDCl$_3$) for sample A is shown in FIG. 1c. The ESI MS spectrum for sample A is set out in FIG. 1d.

Sample B

Figure 2A:
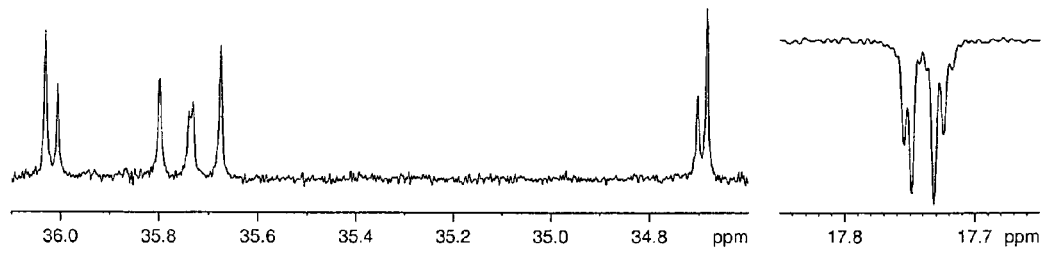
FIGS. 2a, 2b and 2c are graphs of NMR spectral data for a group of compounds of the present invention all having a hexacyclic structure.
Figure 2B:
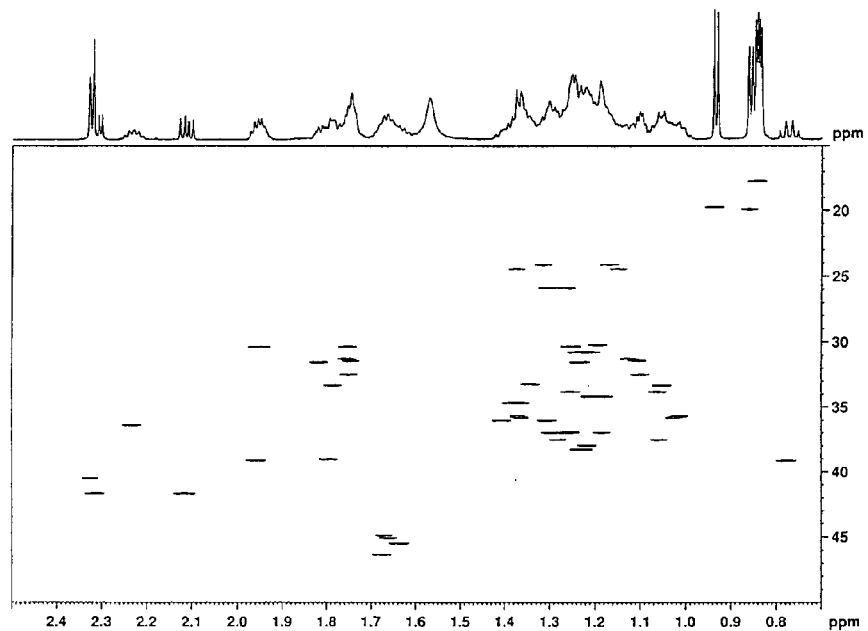
Figure 2C:
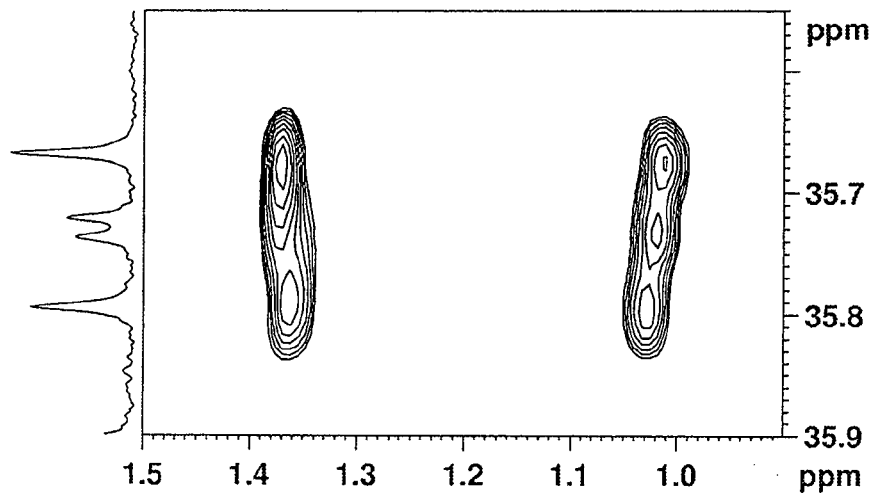
Figure 2D:
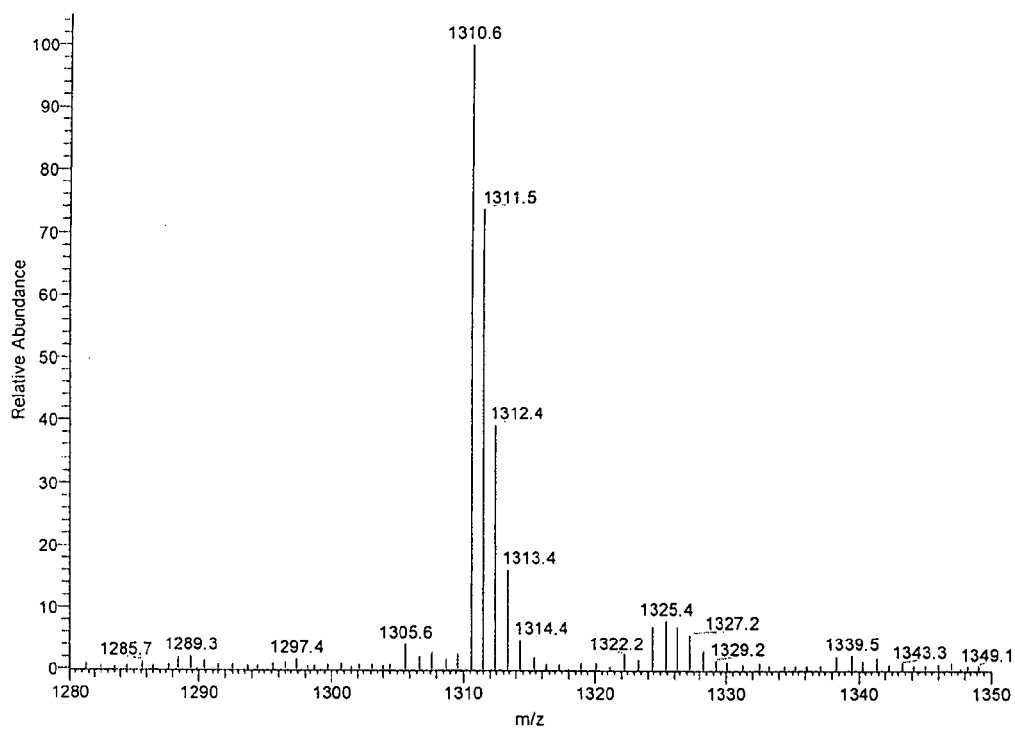
FIG. 2d is a graph of ESI MS data for the compounds of FIGS. 2a to 2c.

The NMR data (800 MHz, CDCl$_3$, 298 K) for sample B are set out in Table 2. The NMR spectra (150 MHz DEPT 35, CDCl$_3$, 298 K) for sample B are shown in FIG. 2a. The HSQC spectra (800 MHz, CDCl$_3$, 298 K) for sample B are shown in FIG. 2b. The HSQC (298 K, CDCl$_3$) spectrum showing the resolution obtained at 600 MHz for sample B is shown in FIG. 2c. The ESI MS spectrum for sample B is set out in FIG. 2d.

TABLE 1

NMR data (800 MHz, CDCl$_3$, 298 K)

| Carbon No. | $\delta_C$ (ppm) | $\delta_H$ (ppm) |
|---|---|---|
| 1 | 173.85$^c$ | |
| 1' | | |
| 2 | 41.69 | 2.11/2.31 |
| 2' | | |
| 3 | 30.36 | 1.95 |
| 3' | | |
| 4 | 36.95 | 1.18/1.30 |
| 4' | | |
| 5 | 25.867 | 1.26/1.30 |
| 5' | 25.871 | |
| 6 | 36.94 | 1.25/1.25 |
| 6' | | |
| 7 | 39.00 | 1.79 |
| 7' | | |
| 8 | 33.322 | 1.05/1.79 |
| 8' | 33.315 | |
| 9 | 31.274 | 1.12/1.75 |
| 9' | 31.281 | |
| 10 | 44.888 | 1.67 |
| 10' | 44.847 | |
| 11 | 38.268 | 1.23 |
| 11' | 38.298 | |
| 12 | 35.73 | 1.02/1.38 |
| 12' | 35.80 | 1.03/1.36 |
| 13 | 24.09 | 1.17/1.32 |
| 13' | 24.42 | 1.15/1.38 |
| 14 | 34.17 | 1.18/1.21 |
| 14' | 37.52 | 1.06/1.28 |
| 15 | 37.96 | 1.22 |
| 15' | 33.21 | 1.34 |
| 16 | 30.74 | 1.21/1.23 |
| 16' | 33.79 | 1.06/1.25 |
| 17 | 19.72 | 0.94 |
| 17' | | |
| 18 | 36.004 | 1.30/1.40 |
| 18' | 36.030 | |
| 19 | 17.754 | 0.84 |
| 19' | 17.748 | |
| 20 | 30.16 | 1.19 |
| 20' | 19.89 | 0.86 |
| 13-Me | | |
| Ome | 51.35 | 3.673 |

From the NMR analysis, the sample A was identified as being a single compound of the general formula (I) set out hereinbefore having 4 cyclic groups and having the following structure:

TABLE 2

NMR data (800 MHz, CDCl$_3$, 298 K) $^a$

| Carbon No. | $\delta_C$ (ppm) | | $\delta_H$ (ppm) |
|---|---|---|---|
| 1 | 173.9 | 173.9 | |
| 1' | | | |
| 2 | 41.69 | 41.69 | 2.32/2.12 |
| 2' | 40.52 | 40.52 | 2.33 |
| 3 | 30.36 | 30.36 | 1.95 |
| 3' | 36.41 | 36.41 | 2.23 |
| 4 | 36.95 | 36.95 | 1.18/1.30 |
| 4' | 31.52 | 31.52 | 1.23/1.82 |
| 5 | 25.873 | 25.867 | 1.26/1.31 |
| 5' | 30.33 | 30.33 | 1.25/1.75 |
| 6 | 36.95 | 36.95 | 1.26/1.26 |
| 6' | 46.346 | 46.352 | 1.67 |
| 7 | 39.01 | 39.01 | 1.80 |
| 7' | 45.512 | 45.518 | 1.63 |
| 8 | 33.322 | 33.315 | 1.05/1.79 |
| 8' | 32.497 | 32.507 | 1.10/1.75 |
| 9 | 31.283 | 31.276 | 1.12/1.75 |
| 9' | 31.43 | 31.43 | 1.10/1.74 |
| 10 | 44.887 | 44.847 | 1.67 |
| 10' | 45.093 | 45.127 | 1.66 |
| 11 | 38.269 | 38.300 | 1.23 |
| 11' | 38.300 | 38.264 | |
| 12 | 35.798 | 35.730 | 1.03/1.36 |
| | | | 1.02/1.36 |
| 12' | 35.674 | 35.739 | 1.01/1.37 |
| | | | 1.02/1.36 |
| 13 | 24.091 | 24.076 | 1.17/1.32 |
| 13' | 24.414 | 24.421 | 1.15/1.37 |
| 14 | 34.173 | 34.159 | 1.18/1.21 |
| 14' | 37.517 | 37.526 | 1.03/1.28 |
| 15 | 37.946 | 37.938 | 1.22 |
| 15' | 33.194 | 33.202 | 1.34 |
| 16 | 30.73 | 30.73 | 1.20/1.23 |
| 16' | 33.773 | 33.787 | 1.06/1.25 |
| 17 | 19.72 | 19.72 | 0.94 |
| 17' | 39.120 | 39.128 | 0.78/1.96 |
| 18 | 36.031 | 36.005 | 1.30/1.40 |
| 18' | 34.684 | 34.703 | 1.37/1.37 |
| 19 | 17.748 | 17.755 | 0.84 |
| 19' | 17.732 | 17.724 | |
| 20 | 30.15 | 30.15 | 1.19 |
| 20' | 19.89 | 19.89 | 0.86 |
| 13-Me | | | |
| Ome | 51.346 | 51.363 | 3.67 |

$^a$ Left $^{13}$C column gives chemical shifts for the major set of signals due to cyclopentyl moiety close to bridge; right $^{13}$C column gives chemical shifts for the minor set of signals due to bicyclopentyl moiety close to the bridge.

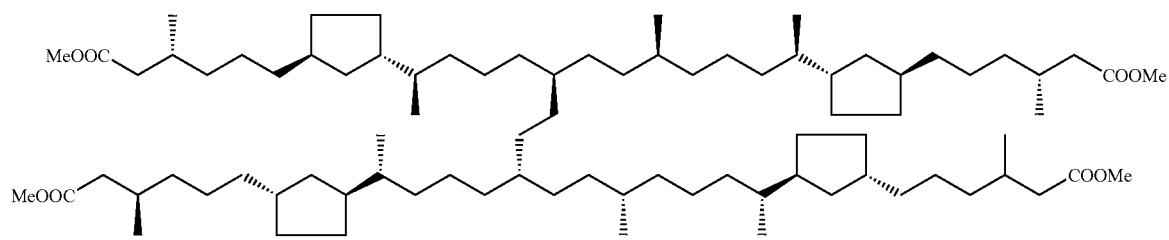 [SMILES: COC(=O)CC(C)CCC[C@H]1CC[C@H]([C@H](C)CCC[C@H](C)CC[C@H](CCC[C@@H](C)[C@H]2CC[C@H](CCC[C@@H](C)CC(=O)OC)C2)CC[C@@H](CCC[C@@H](C)[C@H]2CC[C@H](CCC[C@@H](C)CC(=O)OC)C2)CC[C@@H](C)CCC[C@@H](C)[C@H]2CC[C@H](CCC[C@@H](C)CC(=O)OC)C2)C1]

From the NMR analysis, the sample B was identified as being a mixture of four compounds of the general formula (I) set out hereinbefore, each having 6 cyclic groups and having the following structures:

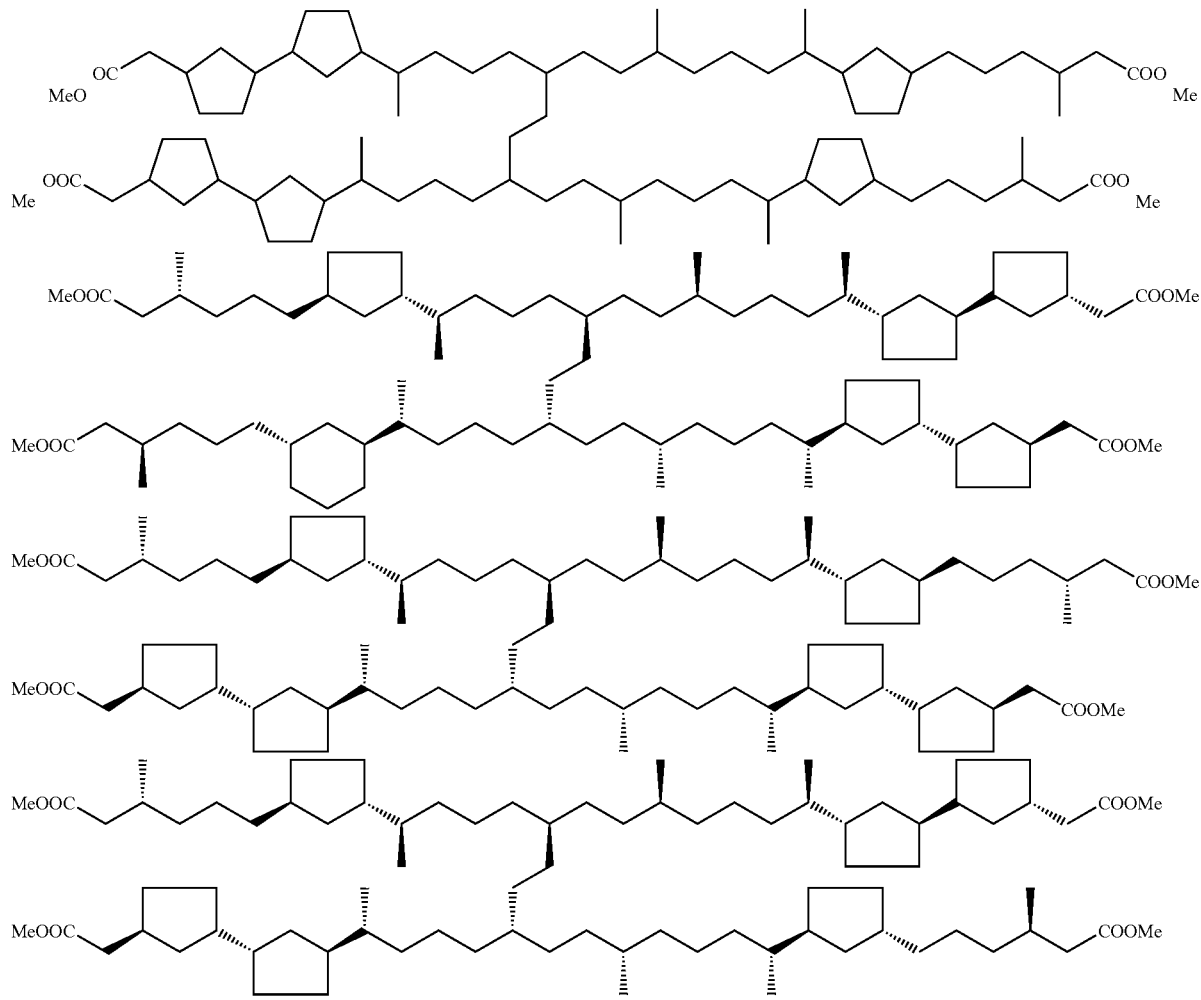

Sample C

Figure 3A:
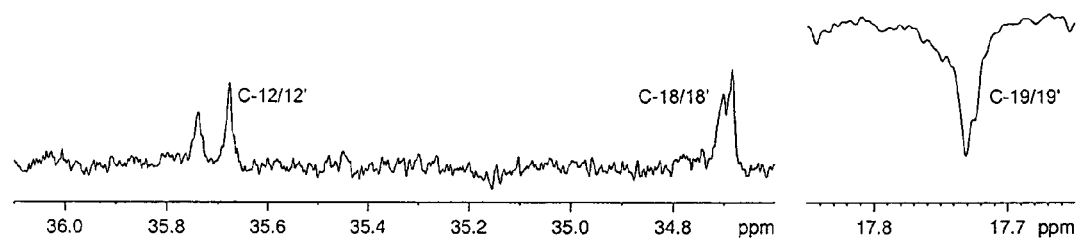
FIG. 3a is a graph of NMR spectral data for a compound of the present invention having an octacyclic structure.
Figure 3B:
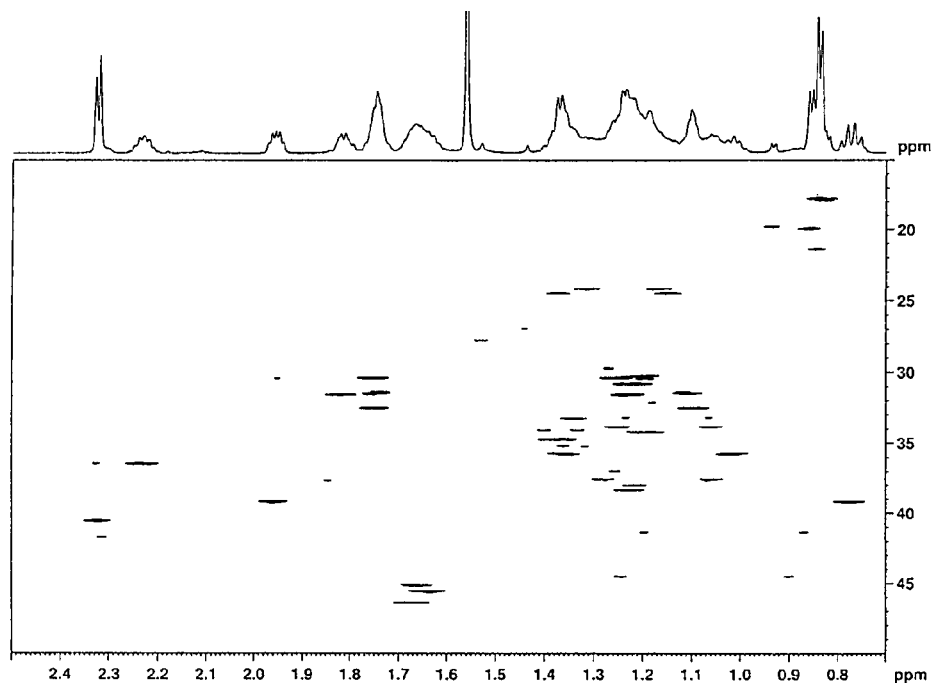
FIGS. 3b and 3c are graphs of NMR spectral data for a group of compounds of the present invention having an octacyclic structure.
Figure 3C:
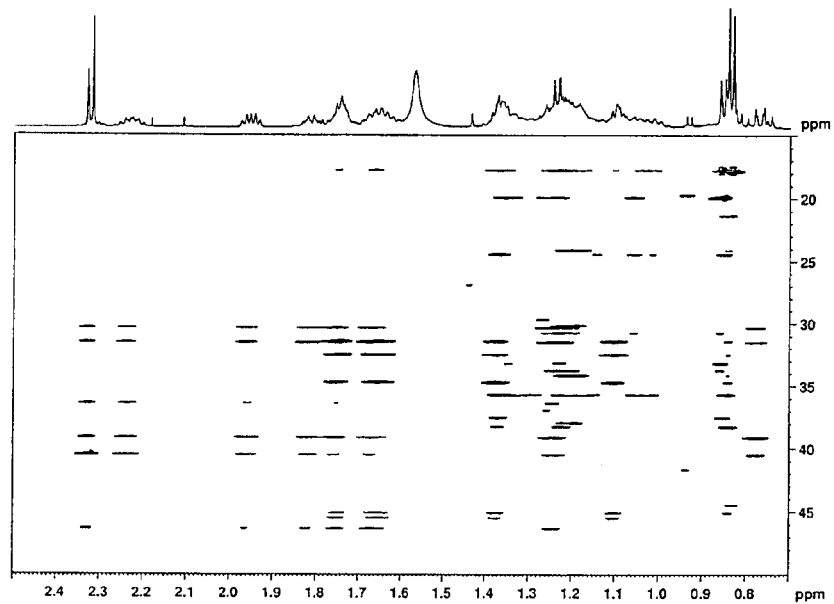
Figure 3D:
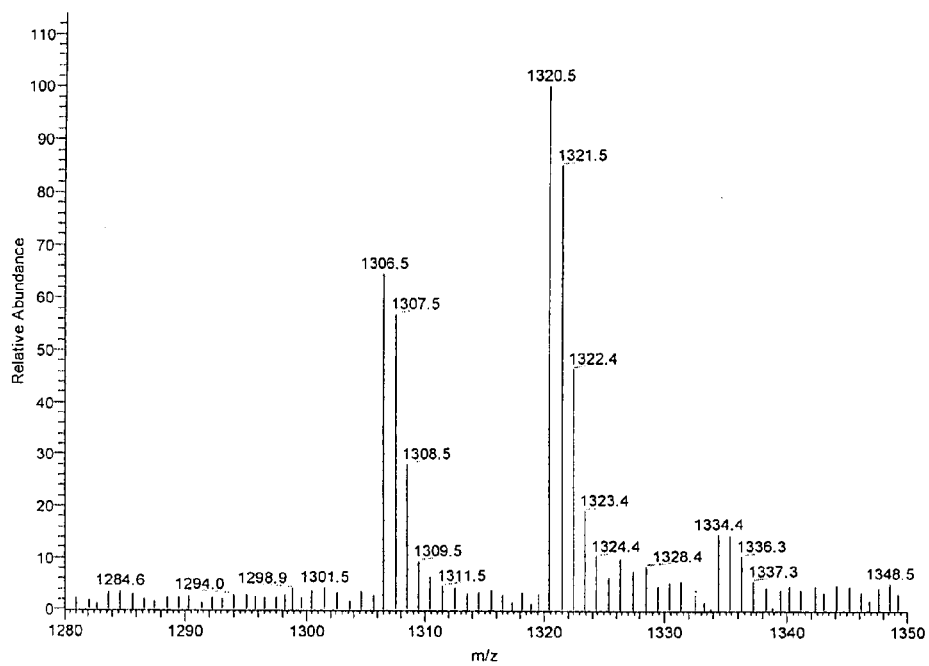
FIG. 3d is a graph of ESI MS data for the group of compounds of FIGS. 3b and 3c.

The NMR data (800 MHz, CDCl$_3$, 298 K) for sample C are set out in Table 3. The NMR spectra (150 MHz DEPT 35, CDCl$_3$, 298 K) for sample C are shown in FIG. 3a. The HSQC spectra (800 MHz, CDCl$_3$, 298 K) for the heavier fraction before separation into samples C to E are shown in FIG. 3b. The 2D TOCSY-HSQC spectrum showing the resolution obtained at 600 MHz (CDCl$_3$, 298 K) for the heavier fraction before separation into samples C to E is shown in FIG. 3c. The ESI MS spectrum for the heavier fraction before separation into samples C to E is set out in FIG. 3d.

TABLE 3

| | NMR data (800 MHz, CDCl$_3$, 298 K) | |
|---|---|---|
| Carbon No. | $\delta_C$ (ppm) | $\delta_H$ (ppm) |
| 1 | 173.87$^c$ | |
| 1' | | |
| 2 | 40.52 | 2.32 |
| 2' | | |

TABLE 3-continued

| | NMR data (800 MHz, CDCl$_3$, 298 K) | |
|---|---|---|
| Carbon No. | $\delta_C$ (ppm) | $\delta_H$ (ppm) |
| 3 | 36.41 | 2.23 |
| 3' | | |
| 4 | 31.52 | 1.23/1.82 |
| 4' | | |
| 5 | 30.34 | 1.25/1.75 |
| 5' | | |
| 6 | 46.344 | 1.67 |
| 6' | 46.351 | |
| 7 | 45.511 | 1.63 |
| 7' | 45.517 | |
| 8 | 32.495 | 1.10/1.75 |
| 8' | 32.505 | |
| 9 | 31.43 | 1.10/1.74 |
| 9' | | |
| 10 | 45.094 | 1.66 |
| 10' | 45.127 | |
| 11 | 38.264 | 1.22 |
| 11' | 38.300 | |
| 12 | 35.676 | 1.01/1.37 |

TABLE 3-continued

| Carbon No. | NMR data (800 MHz, CDCl₃, 298 K) | |
|---|---|---|
| | $\delta_C$ (ppm) | $\delta_H$ (ppm) |
| 12' | 35.738 | 1.02/1.36 |
| 13 | 24.09 | 1.16/1.31 |
| 13' | 24.41 | 1.14/1.37 |
| 14 | 34.16 | 1.18/1.20 |
| 14' | 37.51 | 1.06/1.28 |
| 15 | 37.94 | 1.21 |
| 15' | 33.19 | 1.34 |
| 16 | 30.73 | 1.21/1.23 |
| 16' | 33.77 | 1.06/1.25 |
| 17 | 39.13 | 0.77/1.96 |
| 17' | | |
| 18 | 34.704 | 1.37/1.37 |
| 18' | 34.683 | |
| 19 | 17.723 | 0.84 |
| 19' | 17.731 | |
| 20 | 30.16 | 1.19 |
| 20' | 19.89 | 0.86 |
| 13-Me | | |
| Ome | 51.36 | 3.667 |

From the NMR analysis, the sample C was identified as being a single compound of the general formula (I) set out hereinbefore, having 8 cyclic groups and having the following structure:

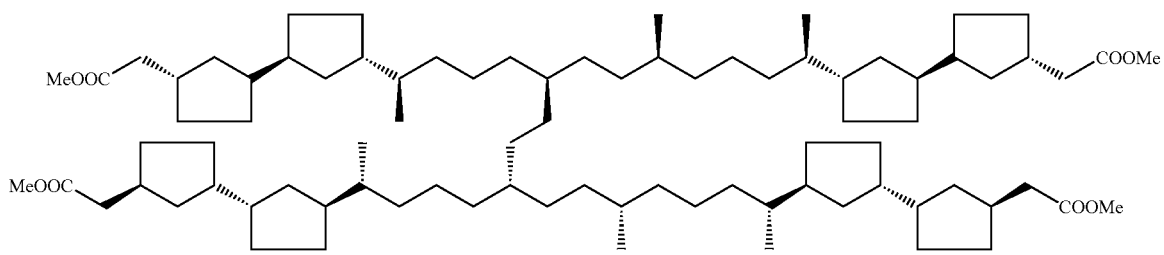

Samples D and E

The NMR data (800 MHz, CDCl₃, 298 K) for sample E are set out in Table 4.

TABLE 4

| Carbon No. | NMR data (800 MHz, CDCl₃, 298 K) [b] | |
|---|---|---|
| | $\delta_C$ (ppm) | $\delta_H$ (ppm) |
| 9 | | |
| 9' | | |
| 10 | 45.03 | 1.68 |
| 10' | | |
| 11 | 35.14 | 1.37 |
| 11' | | |
| 12 | 44.46 | 0.90/1.24 |
| 12' | | |
| 13 | 27.71 | 1.53 |
| 13' | | |
| 14 | 41.33 | 0.87/1.20 |
| 14' | | |
| 15 | 35.19 | 1.32 |
| 15' | | |
| 16 | | |
| 16' | | |
| 17 | | |
| 17' | | |
| 18 | | |
| 18' | | |
| 19 | 17.85 | 0.83 |
| 19' | | |
| 20 | | |
| 20' | | |
| 13-Me | 21.33 | 0.84 |
| OMe | | |

[b] Only shift data for positions with significant changes in chemical shifts compared to the data in Table 3 are given.

From the NMR analysis, the samples D and E were each identified as being a single compound of the general formula (I) set out hereinbefore, having 8 cyclic groups and having the following structures:

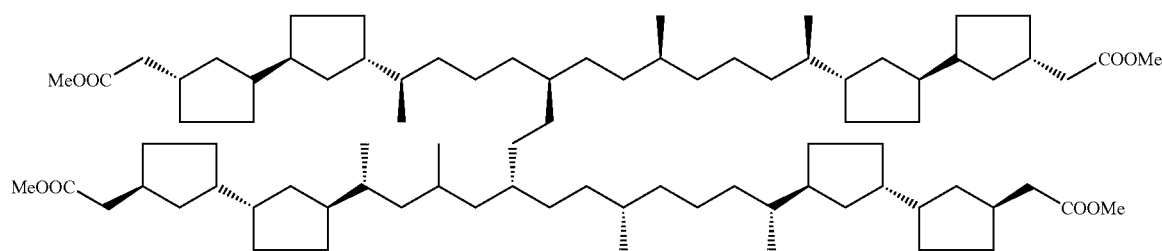

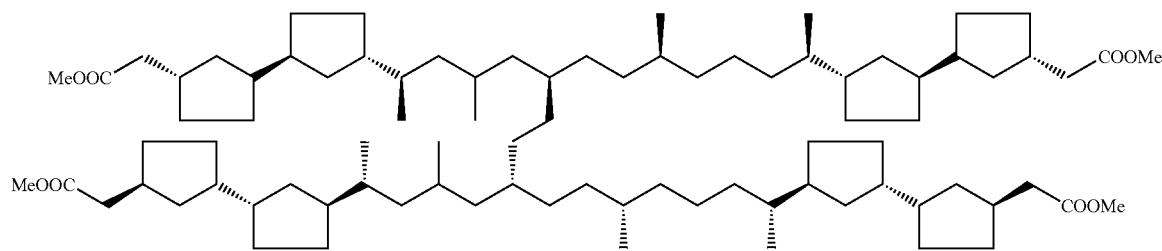

Example 3

Preparation of Liposomes

The compounds isolated and identified in Examples 1 and 2 are used to prepare liposomes according to the following procedure:

The compound (50 mg) is dried using a nitrogen stream, after which the dried sample is added to water (deionised; 5.0 ml). The resulting mixture was heated to 65° C. for 3 hours. After this time, liposome vesicules are to be found in the aqueous mixture. The size of the vesicules may be reduced to the desired size by sonication. Typical vesicules have a diameter of from 50 to 100 nm. The vesicules are dried, for example by freeze drying, following which they are re-hydrated in phosphate buffered saline solution (PBS, 10 mM potassium phosphate, 160 mM sodium chloride, pH 7.1). The lipsome suspension is then filter-sterilised using known techniques. Active ingredient to be contained with the finished liposome may be added to initial aqueous suspension of liposomes or to the PBS solution before rehydration, as required.

The invention claimed is:

1. An isoprenoid according to the general formula (I):

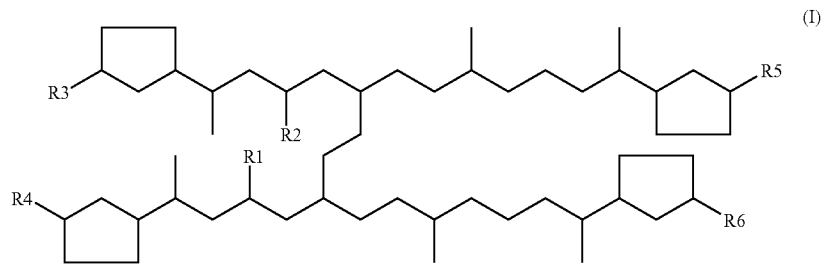

wherein $R_1$ and $R_2$ are independently selected from H and alkyl, with at least one of $R_1$ and $R_7$ being alkyl; and $R_3$, $R_4$, $R_5$ and $R_6$ are variables substituted for by alkyl groups independently selected from groups of the general formula (II) and (III):

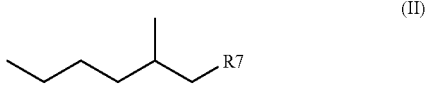

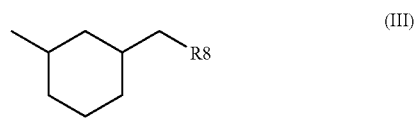

wherein $R_7$ and $R_8$ each represent a group of general formula CO—$R_9$, in which each $R_9$ is independently selected from H, OH, alkyl and alkoxy groups, or $R_7$ and/or $R_8$ present in $R_3$ and $R_4$ and/or in $R_5$ and $R_6$ combine to form a group of the general formula (IV):

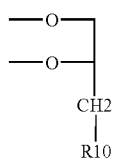

wherein $R_{10}$ is selected from OH and alkoxy; or salts thereof.

2. An isoprenoid according to claim 1, wherein alkyl and alkoxy groups have from 1 to 4 carbon atoms.

3. An isoprenoid according to claim 1, wherein all $R_7$ and/or $R_8$ groups present are the same group.

4. An isoprenoid according to claim 1, wherein at least one of $R_1$ and $R_2$ is hydrogen.

5. An isoprenoid according to claim 1, wherein one of $R_1$ and $R_2$ is hydrogen and the other of $R_1$ and $R_2$ is lower alkyl.

6. An isoprenoid according to claim 1, wherein $R_3$ and $R_5$ are both groups of general formula (II) and wherein both $R_7$ present in the groups of general formula (II) are groups of the general formula CO—$R_9$ in which $R_9$ is H, OH, methyl or methoxy.

7. An isoprenoid according to claim 6, wherein both $R_7$ are the same.

8. An isoprenoid according to claim 1, wherein $R_3$ and $R_4$ are both groups of general formula (II), and wherein both $R_7$ present in the groups of general formula (II) are groups of the general formula CO—$R_9$ in which $R_9$ is H, OH, methyl or methoxy.

9. An isoprenoid according to claim 8, wherein both $R_7$ are the same.

10. An isoprenoid according to claim 1, wherein $R_3$ and $R_6$ are both groups of general formula (II), and wherein both $R_7$ present in the groups of general formula (II) are groups of the general formula CO—$R_9$ in which $R_9$ is H, OH, methyl or methoxy.

11. An isoprenoid according to claim 10, wherein both $R_7$ are the same.

12. An isoprenoid according to claim 1, wherein $R_3$, $R_4$, $R_5$ and $R_6$ are all groups of general formula (II), and wherein all $R_7$ present in the groups of general formula (II) are groups of the general formula CO—$R_9$ in which $R_9$ is H, OH, methyl or methoxy.

13. An isoprenoid according to claim 12, wherein all $R_7$ are the same.

14. An isoprenoid according to claim 1, wherein $R_5$ and $R_6$ are both groups of general formula (III), wherein both $R_8$ present in the groups of general formula (III) are groups of the general formula CO—$R_9$ in which $R_9$ is H, OH, methyl or methoxy.

15. An isoprenoid according to claim 14, wherein both $R_8$ are the same.

16. An isoprenoid according to claim 1, wherein $R_4$ and $R_6$ are both groups of general formula (III), and wherein both $R_8$ present in the groups of general formula (III) are groups of the general formula CO—$R_9$ in which $R_9$ is H, OH, methyl or methoxy.

17. An isoprenoid according to claim 16, wherein both $R_8$ are the same.

18. An isoprenoid according to claim 1, wherein $R_3$ and $R_5$ are both groups of general formula (III), and wherein both $R_8$ present in the groups of general formula (III) are groups of the general formula CO—$R_9$ in which $R_9$ is H, OH, methyl or methoxy.

19. An isoprenoid according to claim 18, wherein both $R_8$ are the same.

20. An isoprenoid according to claim 1, wherein $R_3$, $R_4$, $R_5$ and $R_6$ are all groups of general formula (III), and wherein all $R_8$ present in the groups of general formula (II) are groups of the general formula CO—$R_9$ in which $R_9$ is H, OH, methyl or methoxy.

21. An isoprenoid according to claim 20, wherein all $R_8$ are the same.

22. An isoprenoid according to claim 1, wherein $R_7$ and/or $R_8$ present in $R_3$ and $R_4$ and/or in $R_5$ and $R_6$ are combined to form a group of the general formula (IV).

* * * * *